US010147205B2

(12) United States Patent
Hu

(10) Patent No.: US 10,147,205 B2
(45) Date of Patent: Dec. 4, 2018

(54) MUSIC-COLOUR SYNAESTHESIA VISUALIZATION METHOD

(71) Applicant: CHINA ACADEMY OF ART, Hangzhou (CN)

(72) Inventor: Guosheng Hu, Hangzhou (CN)

(73) Assignee: CHINA ACADEMY OF ART, Hangzhou (CN)

( * ) Notice: Subject to any disclaimer, the term of this patent is extended or adjusted under 35 U.S.C. 154(b) by 0 days.

(21) Appl. No.: 15/572,165

(22) PCT Filed: May 19, 2016

(86) PCT No.: PCT/CN2016/082586
§ 371 (c)(1),
(2) Date: Nov. 7, 2017

(87) PCT Pub. No.: WO2017/000698
PCT Pub. Date: Jan. 5, 2017

(65) Prior Publication Data
US 2018/0144508 A1 May 24, 2018

(30) Foreign Application Priority Data

Jun. 30, 2015 (CN) .......................... 2015 1 0371315

(51) Int. Cl.
*G09G 5/02* (2006.01)
*G06T 11/00* (2006.01)
(Continued)

(52) U.S. Cl.
CPC ............ *G06T 11/001* (2013.01); *G06F 19/00* (2013.01); *G10H 1/0008* (2013.01); *G10H 1/383* (2013.01);
(Continued)

(58) Field of Classification Search
None
See application file for complete search history.

(56) References Cited

U.S. PATENT DOCUMENTS 5,812,688 A * 9/1998 Gibson ................ G10H 1/0008
381/119
6,470,314 B1 * 10/2002 Dharanipragada ..... G10L 15/07
704/231
(Continued)

FOREIGN PATENT DOCUMENTS

| CN | 101702316 A | 5/2010 |
| CN | 104464741 A | 3/2015 |
| CN | 105205304 A | 12/2015 |

*Primary Examiner* — Anh-Tuan V Nguyen
(74) *Attorney, Agent, or Firm* — Gokalp Bayramoglu

(57) ABSTRACT

A visualization method for music-color synesthesia, belonging to the fields of cognitive psychology, color science and computer graphics, and relating to the visualization of the music synesthesia correlation of colors and the generation of a musical color combination scheme. In the method, a musical scale system is presented in the form of a color scale system, and the musical elements are presented through the color correlation to realize the synesthetic conversion between colors and musical elements, and on this basis, a color graphical conversion of the musical structure is performed. The implementations include: a conversion from colors to musical scales, a conversion from colors to chords, a conversion from colors to rhythm and a conversion from colors to texture etc.

8 Claims, 4 Drawing Sheets

(51) Int. Cl.
*G06F 19/00* (2018.01)
*G10H 1/00* (2006.01)
*G10H 1/38* (2006.01)
(52) U.S. Cl.
CPC . *G10H 2210/061* (2013.01); *G10H 2210/066* (2013.01); *G10H 2210/571* (2013.01); *G10H 2220/005* (2013.01); *G10H 2220/021* (2013.01); *G10H 2220/131* (2013.01); *G10H 2220/411* (2013.01)

(56) References Cited

U.S. PATENT DOCUMENTS

| | | | |
|---|---|---|---|
| 2003/0125566 A1 | 7/2003 | Braun | |
| 2009/0177611 A1* | 7/2009 | Savage | G06Q 10/06 706/52 |
| 2011/0096073 A1* | 4/2011 | Adhikari | G06T 15/005 345/426 |
| 2011/0191674 A1* | 8/2011 | Rawley | G06F 3/016 715/702 |
| 2013/0215394 A1* | 8/2013 | Reddy | G09G 5/10 353/31 |
| 2016/0142830 A1* | 5/2016 | Hu | G02C 11/06 434/185 |

* cited by examiner

| | | C | #C | D | #D | E | F | #F | G | #G | A | #A | B | C |
|---|---|---|---|---|---|---|---|---|---|---|---|---|---|---|
| pigment, printing | hue values of octave circulation | 0 | 20 | 32 | 46 | 56 | 79 | 158 | 192 | 208 | 233 | 278 | 322 | 0 |
| light color, screen | | 0 | 30 | 60 | 90 | 120 | 150 | 180 | 210 | 240 | 270 | 300 | 330 | 0 |
| great musical scale | purity value | 38 | 39 | 40 | 41 | 42 | 43 | 44 | 45 | 46 | 47 | 48 | 49 | 50 |
| | brightness value | 0 | 2 | 4 | 6 | 8 | 10 | 12 | 14 | 16 | 18 | 20 | 22 | 24 |
| small musical scale | purity value | 50 | 51 | 52 | 53 | 54 | 55 | 56 | 57 | 58 | 59 | 60 | 61 | 62 |
| | brightness value | 24 | 26 | 28 | 30 | 32 | 34 | 36 | 38 | 40 | 42 | 44 | 46 | 48 |
| one-lined octave | purity value | 62 | 63 | 64 | 65 | 66 | 67 | 68 | 69 | 70 | 71 | 72 | 73 | 74 |
| | brightness value | 48 | 50 | 52 | 54 | 56 | 58 | 60 | 62 | 64 | 66 | 68 | 70 | 72 |
| two-lined octave | purity value | 74 | 75 | 76 | 77 | 78 | 79 | 80 | 81 | 82 | 83 | 84 | 85 | 86 |
| | brightness value | 72 | 74 | 76 | 78 | 80 | 82 | 84 | 86 | 88 | 90 | 92 | 94 | 96 |

Figure 1

| chord names | composition tone | tonic (I) | mediant (III) | dominant (V) | other tones |
|---|---|---|---|---|---|
| major triad (I) | I, III, V | H0, S62, B48 | H120, S66, B56 | H210, S69, B62 | |
| minor triad (I m) | I, ♭III, V | H0, S62, B48 | H90, S65, B54 | H210, S69, B62 | |
| augmented triad (I aug) | I, III, ♯V | H0, S62, B48 | H120, S66, B56 | H240, S70, B64 | |
| diminished triad (I dim) | I, ♭III, ♭V | H0, S62, B48 | H90, S65, B54 | H180, S68, B60 | |
| suspended fourth chord (I sus4) | I, V, IV | H0, S62, B48 | | H210, S69, B62 | H150, S67, B58 |
| major sixth chord (I 6) | I, III, V, VI | H0, S62, B48 | H120, S66, B56 | H210, S69, B62 | H270, S71, B66 |
| minor sixth chord (I m6) | I, ♭III, V, VI | H0, S62, B48 | H90, S65, B54 | H210, S69, B62 | H270, S71, B66 |
| major minor seventh chord (I 7) | I, III, V, ♭VII | H0, S62, B48 | H120, S66, B56 | H210, S69, B62 | H300, S72, B68 |
| minor seventh chord (I m7) | I, ♭III, V, ♭VII | H0, S62, B48 | H90, S65, B54 | H210, S69, B62 | H300, S72, B68 |
| major seventh chord (I maj7) | I, III, V, VII | H0, S62, B48 | H120, S66, B56 | H210, S69, B62 | H330, S73, B70 |
| major seventh flat five chord (I 7-5) | I, III, ♭V, ♭VII | H0, S62, B48 | H120, S66, B56 | H180, S68, B60 | H300, S72, B68 |
| minor seventh flat five chord (I m7-5) | I, ♭III, ♭V, ♭VII | H0, S62, B48 | H90, S65, B54 | H180, S68, B60 | H300, S72, B68 |
| diminished seventh chord (I dim7) | I, ♭III, ♭V, ♭♭VII | H0, S62, B48 | H90, S65, B54 | H180, S68, B60 | H270, S71, B66 |

Figure 2

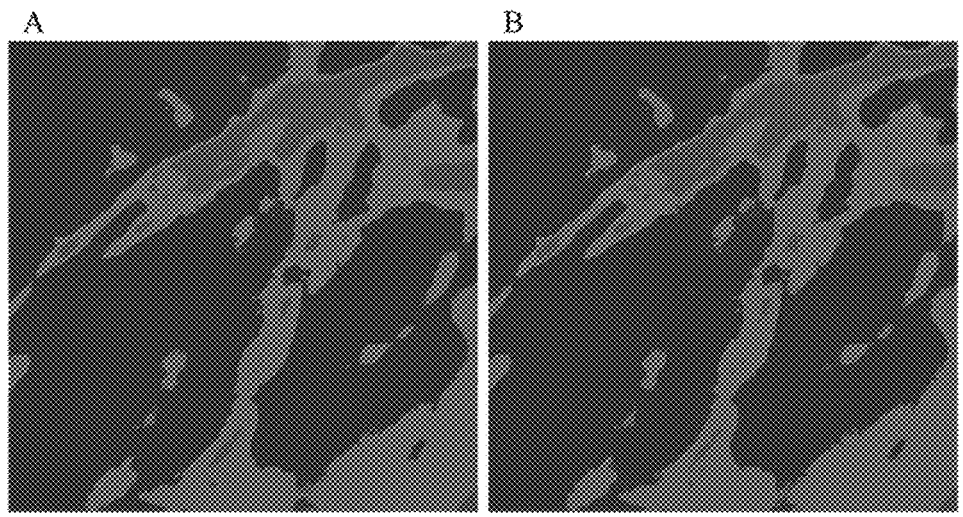

Figure 3

MUSIC-COLOUR SYNAESTHESIA VISUALIZATION METHOD

CROSS REFERENCE TO RELATED APPLICATIONS

This application is the national phase entry of International Application No. PCT/CN2016/082586, filed on May 19, 2016, which is based upon and claims priority to Chinese Patent Application No. 201510371315.1 filed on Jun. 30, 2015, the entire contents of which are incorporated herein by reference.

TECHNICAL FIELD

The present invention belongs to the fields of cognitive psychology, color science and computer graphics, and relates to the visualization of the music synesthesia relation of colors and the generation method of a music-color combination scheme.

BACKGROUND

There is a close recognition relation between music and color, which have a synesthesia correlation in the hearing and vision of the human beings. However, most of the existing achievements relate to the substantial theoretical confirmation and description of the synesthesia correlation, and there is a lack of synesthesia conversion method that can be used in engineering realization.

The existing definition and principle of the music-color synesthesia correlation are mainly directed to the conceptual correspondence between the tone and hue. These theories not only lack concrete quantitative methods, but also cannot form a complete system in combination with the factors such as the purity and brightness of color and the like. Also, by using these theories, the correlation of the tone circulation and the musical scale superposition, and other more complex constitutive factors synthesized by sounds, harmony, melody, texture etc., cannot be deconstructed. Therefore, based on the existing theories, the systematized implementation and application of music-color visualization. cannot be realized.

The present invention provides a music-scaled color synesthesia mapping principle, and on this basis, a comprehensive factor estimating method for the music-color visualization is further provided, which is considered as the basic technology of the music-color visualization. The music-color visualization method of the present system can be used in the fields of media interaction, artistic creation, intelligent design etc. across sound and image.

SUMMARY OF THE INVENTION

The present invention is a music-oriented color synesthesia visualization method. The estimating method of music-scaled color sequence is the basis of the present invention and the method includes the following principles.

According to different presentation media, the three hue value schemes shown in the following table including a pigment or printing, a screen presentation and a colored light mixing are used accordingly; and for the medium of pigment or printing and the medium of screen presentation, a HSL/HSB color mode is used. Moreover, for the colored light mixing, hues corresponding to tones $^{\#}A(^{b}B)$ and B are mixed by red light with a wavelength of 650 nm and blue light with a wavelength of 428 nm, respectively. A ratio of the red light to the blue light for the tone of $^{\#}A(^{b}B)$ is 1:2, and a ratio of the red light to the blue light for the tone of B is 2:1. Each of the three hue value schemes satisfy the principle that the hue values corresponding to the musical scales are repeated per octave, namely, the hue values corresponding to each octave are cycled on the hue circle. According to the above-mentioned estimating method of hue, a corresponding angle of each musical scale on the HSL or HSB hue circle can be synchronously adjusted in a range of −15 degrees to +15 degrees. When the evaluation is performed based on the length of light wave, a corresponding wavelength of each color scale can be adjusted in a range of −18 nm to +18 nm.

TABLE 1 degree and colored light wavelength of each tone in different modes

| Corresponding tone | C | $^{\#}C/^{b}D$ | D | $^{\#}D/^{b}E$ | E | F | $^{\#}F/^{b}G$ | G | $^{\#}G/^{b}A$ | A | $^{\#}A/^{b}B$ | B |
|---|---|---|---|---|---|---|---|---|---|---|---|---|
| Pigment or printing mixing | 0° | 20° | 32° | 46° | 56° | 79° | 158° | 192° | 208° | 233° | 278° | 322° |
| Screen presentation | 0° | 30° | 60° | 90° | 120° | 150° | 180° | 210° | 240° | 270° | 300° | 330° |
| Colored light wavelength (nm) | 650 | 631 | 610 | 589 | 566 | 541 | 515 | 488 | 459 | 428 | mixed by red light and blue light | |

For the modes of pigment mixing & printing output or screen presentation, a minimum value and a maximum value are respectively selected on each of a purity axis and a brightness/lightness axis of a HSL or a HSV color solid. Moreover, an interval between the minimum value and the maximum value is equally divided according to the total number of color scales, namely, the corresponding purity value and brightness value of each color scale are set based on the principle of equidifferent gradient. The total number of color scales is determined according to a vocal range span or the number of superimposing times of an octave. Moreover, by respectively controlling the maximum value and the minimum value of the purity and brightness/lightness, a total span of a corresponding color scale sequence and the purity and brightness/lightness of each color corresponding to each musical scale are adjusted to simulate a variation of timbre features based on the overall variation of the color scale sequence. With reference to the hue value determined by the tone and the purity value and brightness/lightness value determined by the pitch, the hue value, the purity value and the brightness/lightness value of each color corresponding to each musical scale are estimated to obtain a color scale sequence corresponding to the musical scale. The color scale sequence has a spiral structure in the HSL or HSB color solid.

For the mode of colored light mixing, an even gradient variation of the brightness/lightness and the saturation is obtained through a mixing ratio of a colored light intensity corresponding to a tone and neutral white light, so as to form a color scale sequence of light. Moreover, the higher the brightness/lightness and brilliance of the colored light, the higher is the corresponding musical scale, and the lower the brightness/lightness and brilliance of the colored light, the lower is the corresponding musical scale. In the same scheme of color scale sequence, the brightness/lightness and the brilliance of the colored light change with an even gradient along with the color scale sequence.

On the basis of the musical-scaled color sequence estimating method, a combination of colors can be provided according to the constitutive principle of the music chord, namely, a corresponding color-chord combination is estimated according to the structure of the music chord. When the color-chord is presented in a graphical form, the area size occupied by each color follows the following order from large to small: the colors corresponding to the tonic, the dominant, the mediant, and the other tones. When a color-chord combination is estimated, the purity value and brightness/lightness value corresponding to each color scale do not change due to the adjustment of the hue value.

When using the colored graphics to realize a visualization of the musical melody, the factors such as opacity, the number of repeated color blocks, length or width of lines, the area occupation, presentation time etc. of each color are directly proportional to a duration of a corresponding note in the melody and inversely proportional to an intensity of a corresponding note in a melody.

When using the colored graphics to realize the visualization of a music texture, a color corresponding to the melody of each voice part constitutes a complete themed graphic object, and a color corresponding to the chord constitutes a background texture without a theme.

When the corresponding music has a plurality of voice parts, a plurality of corresponding themed graphics act in cooperation with each other in the image.

For the music having different pitches, with reference to the method for estimating a music structure according to the pitch in the music. Similarly, a specific color combination of corresponding color scale, chord, melody and texture etc. is estimated.

The calculation method of color data of the present invention is based on HSL, HSP (HSV) color mode and light color mixing mode respectively. Also, the present invention can be realized by converting the color mode into a CMYK color mode for printing output or pigment mixing.

BRIEF DESCRIPTION OF THE DRAWINGS

FIG. 1 shows the color element values corresponding to a four-octave color sequence.

FIG. 2 shows the common color chord combination of a one-lined octave C-key based on the color scale scheme shown in FIG. 1.

FIG. 3 is a color combination graphic of a C major with triad.

DETAILED DESCRIPTION OF THE INVENTION

Figure 4:
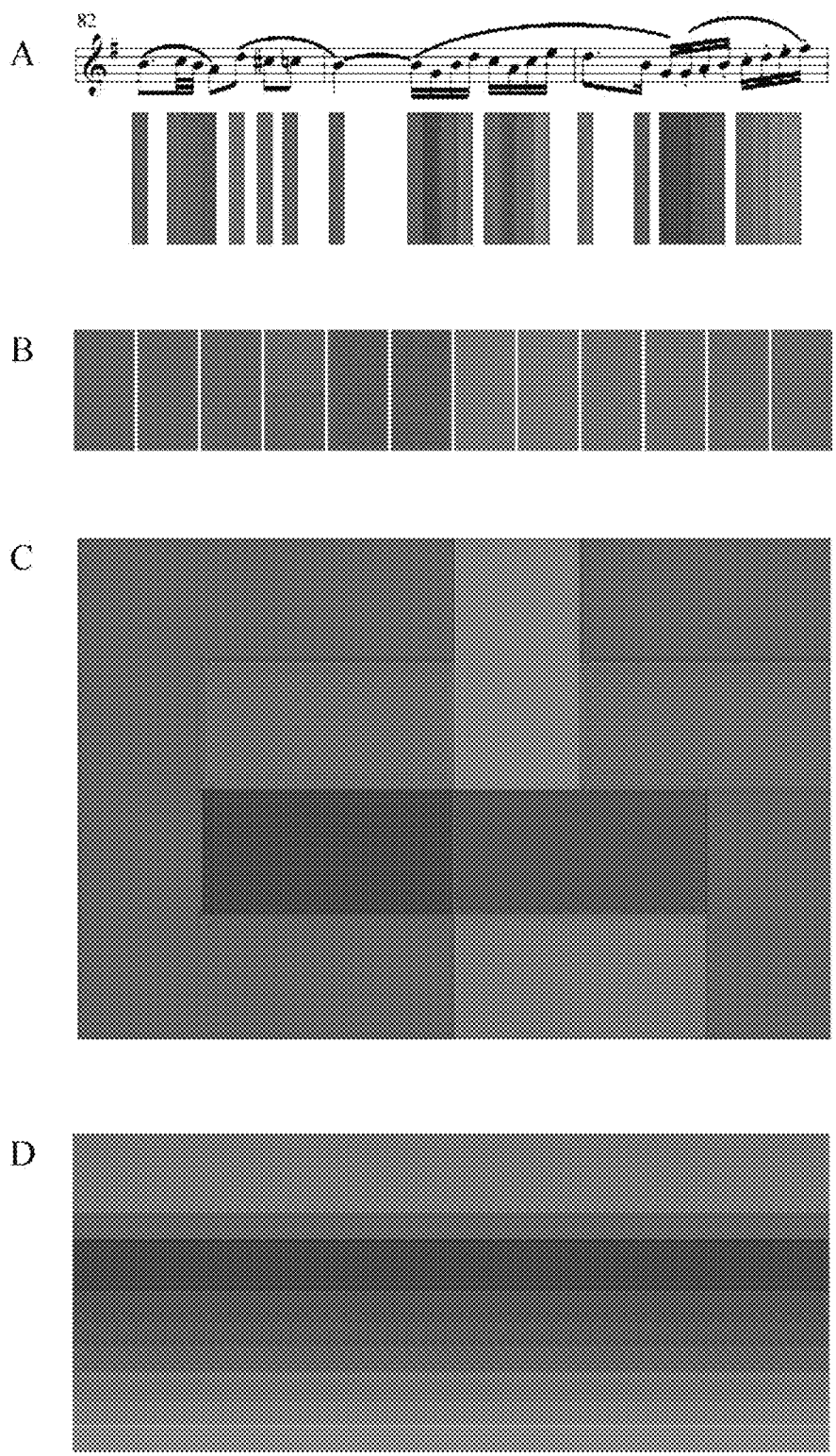
FIG. 4 is an example of a melody color visualization corresponding to a music segment.

Hereinafter, a specific embodiment of the present invention in a HSB color mode will be described with reference to the drawings. It should be noted that the following embodiments are merely illustrative examples, and the present invention is not limited to the scope of the following embodiments.

In the HSB color mode, the music-scaled color sequence estimating method includes a synchronous musical-scale sequence evaluation of the hue, the purity and the brightness/lightness. Moreover, the dimensions of these three elements are repeatedly superimposed with the estimated values. Further, two estimating principles, the pigment (printing) and the screen presentation, are respectively used as the evaluation methods of the hue value according to the different color presentation media. Also, a hue value corresponding to an octave higher of a tone completely equals to a hue vale corresponding to an octave lower of the tone. Each octave corresponds to a cycle on the hue circle.

The estimating method of purity and brightness/lightness values is as follows: setting a minimum value intersection point of the purity and the brightness, and a maximum value intersection point of the purity and the brightness on a purity-brightness section of the HSB color space, respectively; connecting the minimum intersection point and the maximum intersection point to form a purity-brightness axis; equally dividing the interval between the minimum value and the maximum value on the purity-brightness axis according to the vocal range of the color sequence, and the coordinate of each dividing point includes the purity value and the brightness value of each corresponding color scale. Moreover, an end of low purity value and brightness value corresponds to the low musical scale, an end of high purity value and brightness value corresponds to the high musical scale. The lowest musical note corresponds to the minimum purity value and brightness value, and the highest musical note corresponds to the maximum purity value and brightness value.

The estimating methods of the hue value, the purity value and the brightness value are combined to form a spiral-shaped color sequence in the HSB color solid space, and the spiral-shaped color sequence is the music-scaled color scale sequence. Moreover, the span and the color property of the color scale sequence are determined by two factors, the vocal range and the timbre. The vocal range covers at least one octave (a total of thirteen chromatic scales) and up to eight octaves (a total of 97 chromatic scales). The possible minimum value of purity and brightness/lightness is 0 and the possible maximum value thereof is 100.

Following the above-mentioned principle, if the vocal range corresponding to a color sequence span covers four octaves, the purity value of a color corresponding to the lowest note is 38, and the brightness/lightness value thereof is 0. Moreover, the purity value of a color corresponding to the highest note is 86, and the brightness/lightness value thereof is 96. The estimated values of the color scale sequence are shown in FIG. 1.

According to the data listed in the above-mentioned table, the HSB values of a color corresponding to the one-lined octave C-key of the musical-scaled color scale sequence are respectively H0, S62 and B48. Except for the C-key note, the hue value of each color scale corresponds to one of two values depending on the light color medium, but the purity value and the brightness/lightness value remain unchanged with different light color media.

Based on the above-mentioned music-scaled color sequence estimating method, the corresponding color combination is matched according to the constituting principle of musical chord. When the music-scaled color scheme covering four octaves as shown in FIG. 1 is used, the main chorded color combination corresponding to a root of one-lined octave C-key.

When the color-chords are presented in a graphical form, the area occupation of each color from large to small follows the following order: the colors corresponding to the tonic, the dominant, the mediant and other tones. FIG. 3 shows a graphical result of the major triad (i.e. the C chord) listed in FIG. 2. Specifically, FIG. 3-A shows the scheme using the screen or light color mode. FIG. 3-B shows the scheme using the pigment mixing and printing output mode. The HSB values of color in FIG. 3-A are respectively: H0, S62, B48; H120 S66, B56; H210, S69, B62. The HSB values of color in FIG. 3-B are respectively; H0, S62, B48 H56, S66, B56; H192, S69, B62.

When the color graphics are used to represent the musical melody, the color composition factors are used to realize the visual representation of musical melody. FIG. 4 is an embodiment of the color visualization of the melodic part of the Mozart C Major Piano Sonata (K.545) Section 82-84 through the composition factors. Specifically, FIG. 4-A shows a music score of the melodic vocal part and the corresponding color of each note. FIG. 4-B shows that the repeating number of color blocks of a color corresponding to each note in section 82 is directly proportional to the duration of the note in the melody. FIG. 4-C shows that an area occupation of a color corresponding to each note in section 83 is directly proportional to the duration of the note in the melody. FIG. 4-D shows that the line width of a color corresponding to each note in section 84 is directly proportional to the duration of the note in the melody.

Figure 5:
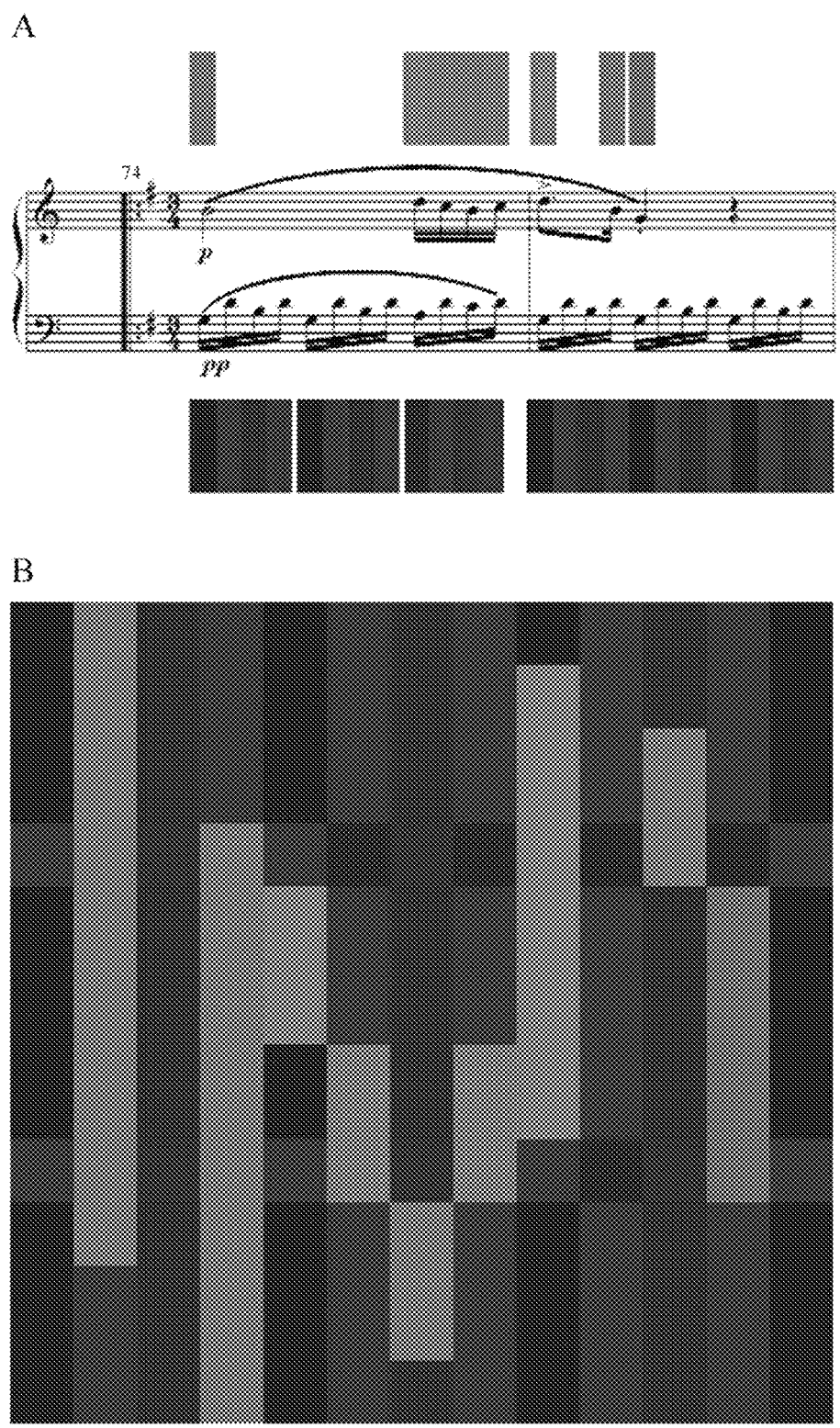
FIG. 5 is an example of a harmonic texture color visualization corresponding to a music segment.

When the color graphics are used to represent the musical texture, the color corresponding to the melody of each voice part constitutes a complete themed graphic object, and the polyphony with multiple voice parts can be represented as an image having multiple themed graphic objects interweaved with each other. Moreover, the color corresponding to chord accompaniment voice part constitutes a background texture without a theme. FIG. 5 is an embodiment of the color visualization of the harmony texture structure of the Mozart C major piano sonata (K.545) Section 74-75. FIG. 5-A shows a music score of the melodic voice part and the color corresponding to each note. FIG. 5-B shows the color visualized graphic of this music segment, wherein the background corresponds to the chord accompaniment voice part, and the theme graphic corresponds to the melodic voice part.

The embodiments of the present specification are merely the examples to implement the inventive concept. The scope of the present invention should not be considered as being limited to the specific implementations described in the embodiments. All equivalent technical means and implementations that can be derived from the inventive concept of the present invention fall within the protection scope.

What is claimed is:

1. A music-color synesthesia visualization method, comprising:
   a music-scaled color scale sequence estimating method, including:
   applying a hue value estimating method in three modes including a pigment or printing, a screen presentation and a colored light mixing according to different presentation media, and setting a hue value corresponding to each tone;
   for the mode of pigment mixing, printing output or screen presentation, respectively dividing an interval between a minimum value and a maximum value on a saturation axis and a brightness/ lightness axis of a HSL or HSB(HSV) color solid according to a total number of color scales, namely, determining a saturation value and a brightness/ lightness value of each color scale according to an equidifferent gradient principle;
   for the mode of pigment mixing, printing output or screen presentation, with reference to a hue value determined by a tone, and the saturation value and the brightness/ lightness value determined by a pitch, estimating the hue, the saturation value and the brightness/ lightness value of a color corresponding to a musical scale on the HSL or HSB color solid to obtain a color scale sequence corresponding to the musical scale;
   for the mode of colored light mixing, forming a light color scale sequence through an even gradient variation of brightness/ lightness and saturation, wherein the even gradient variation is obtained by a mixing ratio of a colored light intensity and neutral white light corresponding to the tone;
   a chorded method for color combination including:
   based on a composition principle of the musical chord, estimating all colors corresponding to each composing note of the chord to form the color combination corresponding to the musical chord;
   a musical melody graphical method including:
   forming a graph of the musical melody for the different presentation media by drawing a corresponding color of each note corresponding to a duration and intensity of the corresponding note in the musical melody;
   wherein the music-scaled color scale sequence estimating method determines the corresponding color of each note; and
   wherein a background texture of the graph of the musical melody includes a color combination corresponding to a chord accompaniment voice part determined by the chorded method.

2. The method of claim 1, wherein the hue value corresponding to each octave cycles one time on a hue circle, and on the saturation axis and the brightness/lightness axis, the total number of the color scales is determined according to a voice range span and the number of superimposing times of an octave.

3. The method of claim 1, wherein on the saturation axis and the brightness/ lightness axis, the maximum value and the minimum value are respectively controlled to adjust a total span of a corresponding color scale sequence and the saturation value and the brightness/ lightness value of a corresponding color of each musical scale, so as to achieve a representation of variation effects of tone by using an overall variation of the color scale sequence.

4. The hue and musical scale estimating method of claim 1, wherein in the mode of pigment mixing, printing output, or screen presentation, a corresponding angle of each musical scale on the HSL or HSB hue circle can be synchronously adjusted in a range of −15 degrees to +15 degrees.

5. The hue and musical scale estimating method of claim 1, when the estimation is performed in the mode of colored light mixing according to a wavelength of light, a corresponding wavelength of each color scale is adjusted in a range of −18 nm to +18 nm.

6. The method of claim 1, wherein when the color chord is shown in a graphic form, the area occupation of each color from large to small follows the following order: colors corresponding to tonic, dominant, mediant and other tones.

7. The method of claim 1, wherein with reference to a method for estimating a music structure according to the pitch in the music, similarly, specific color combinations of color scale, chord, melody and texture are estimated.

8. The method of claim 1, when based on a HSL or HSB color mode, and being used for printing, output and pigment mixing, the HSL or HSB color mode can be converted into CMYK color mode.

* * * * *